US005649926A

United States Patent [19]
Howland

[11] Patent Number: 5,649,926
[45] Date of Patent: Jul. 22, 1997

[54] SPINAL SEGMENTAL REDUCTION DEROTATIONAL FIXATION SYSTEM

[75] Inventor: Robert S. Howland, Seal Beach, Calif.

[73] Assignee: Advanced Spine Fixation Systems, Inc., Irvine, Calif.

[21] Appl. No.: 467,613

[22] Filed: Jun. 6, 1995

Related U.S. Application Data

[62] Division of Ser. No. 274,971, Jul. 14, 1994.

[51] Int. Cl.[6] .................................................. A61B 17/56
[52] U.S. Cl. ............................ 606/61; 606/73; 606/72
[58] Field of Search ........................... 606/60, 61, 53–59, 606/72, 73; 411/392, 383, 389, 378

[56] References Cited

U.S. PATENT DOCUMENTS 2,696,817  12/1954  Prevo ........................................ 606/72
5,034,011   7/1991  Howland .................................. 606/61
5,047,029   9/1991  Aebi et al. ............................... 606/61
5,053,034  10/1991  Olerud ..................................... 606/60
5,129,900   7/1992  Asher et al. .............................. 606/72
5,254,118  10/1993  Mirkovic .................................. 606/61

*Primary Examiner*—Michael Buiz
*Assistant Examiner*—Mark S. Leonardo
*Attorney, Agent, or Firm*—Christie, Parker & Hale, LLP

[57] ABSTRACT

The present invention relates to a spinal fixation system. The system comprises a screw for pivotally attaching a bolt to a vertebrae to be treated. A pivot block is threaded onto the bolt to move the pivot block up and down the bolt. A rod is secured at each of its ends to vertebrae on either side of the vertebrae to be treated and a clamp block is attached to the rod and the pivot block to thereby allow the pivot block to push, pull or rotate the vertebrae to be treated.

4 Claims, 5 Drawing Sheets

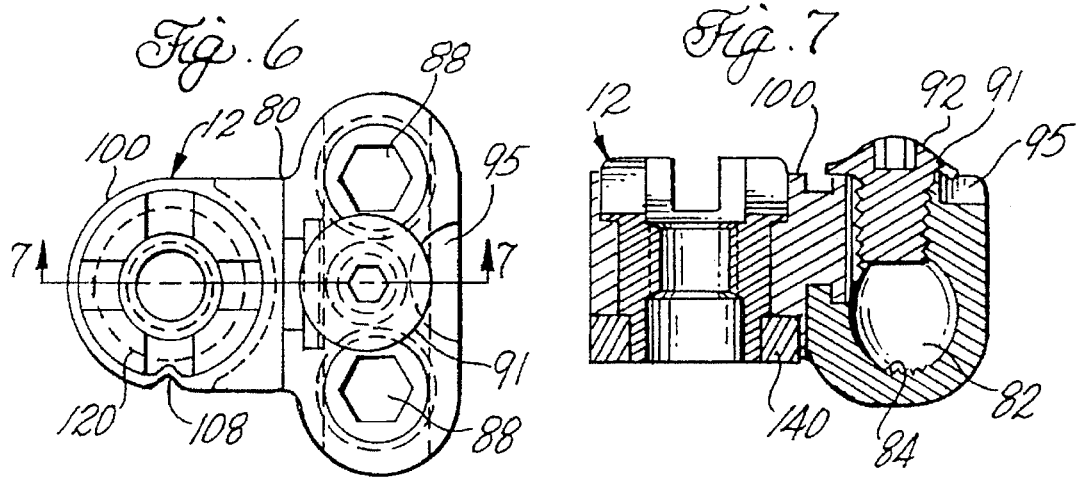
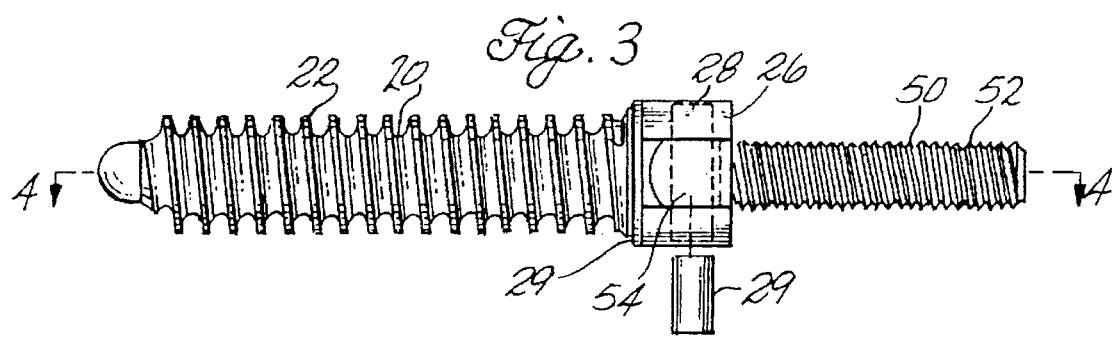
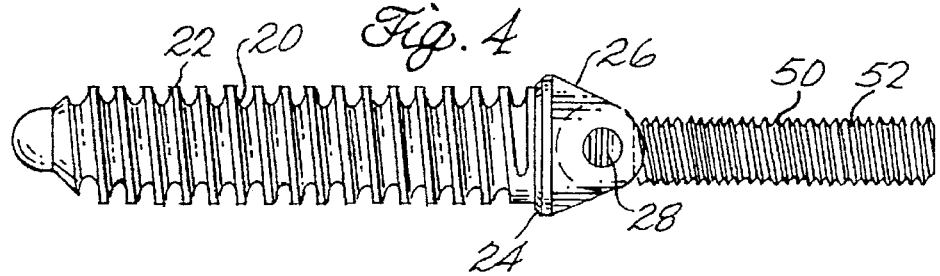
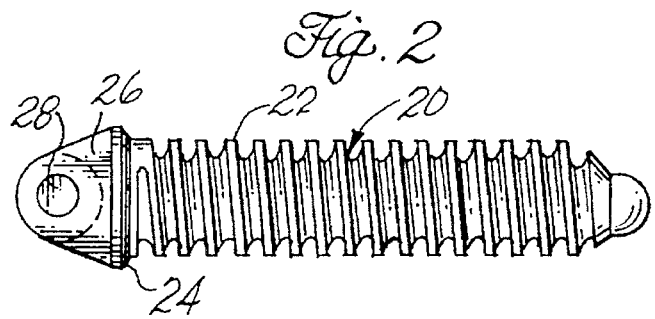

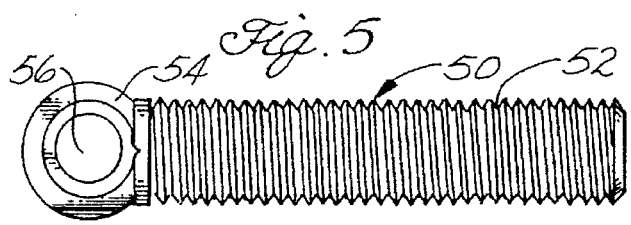
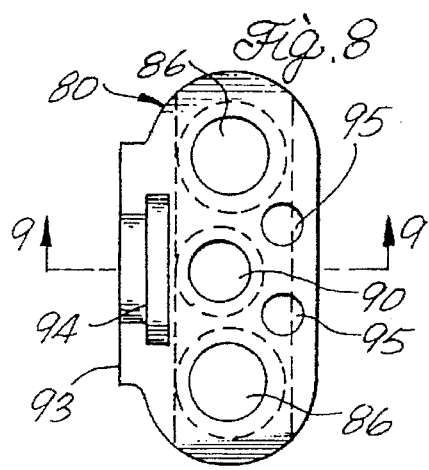
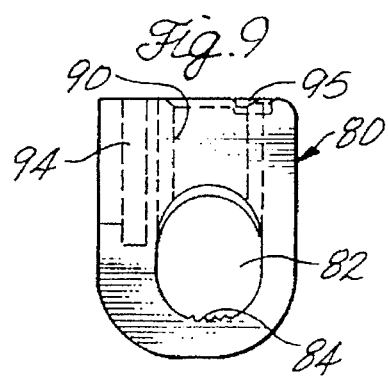
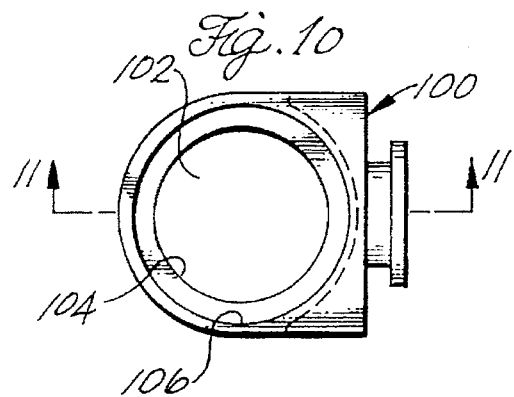
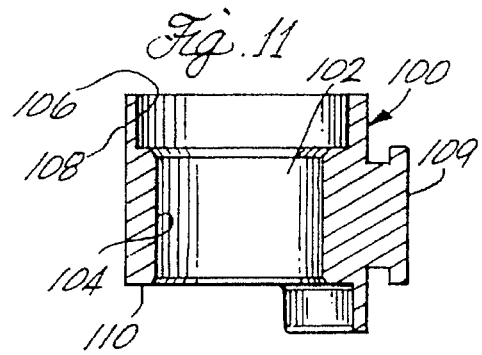
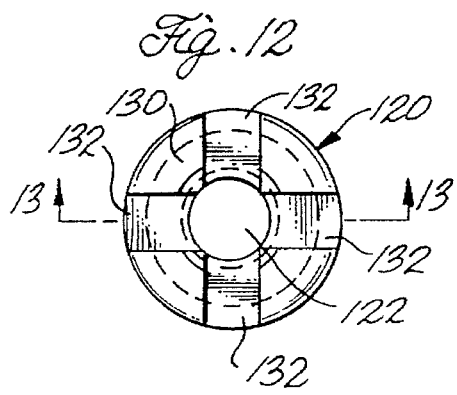
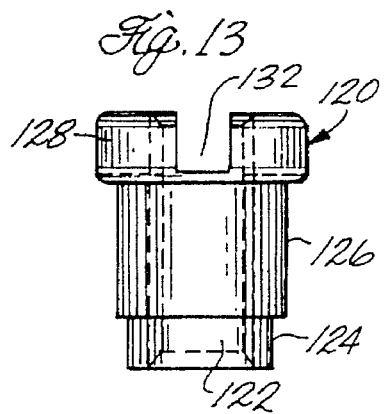

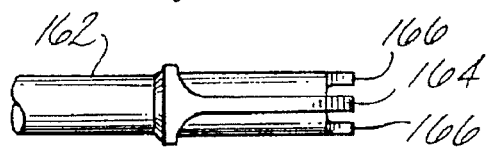

5,649,926

SPINAL SEGMENTAL REDUCTION DEROTATIONAL FIXATION SYSTEM

CROSS-REFERENCE TO RELATED APPLICATION

This is a division of application Ser. No. 08/274,971, filed Jul. 14, 1994, pending, which is incorporated herein by reference.

FIELD OF THE INVENTION

This invention relates to an implantable spinal fixation device for the surgical treatment of spinal disorders which may require correction, stabilization, adjustment or fixation of the spinal column, in particular this invention relates to a clamped rotating spindle assembly for pushing, pulling or rotating vertebrae back into alignment with the spine.

BACKGROUND OF THE INVENTION

Various types of spinal column disorders are known and include scoliosis (abnormal curvature or rotation of vertebrae relative to the plane of the spine), kyphosis (abnormal backward curvature of the spine) and spondylolisthesis (forward displacement of a lumbar vertebra), all of which involve a "misalignment" of the spinal column. Patients who suffer from such conditions usually experience extreme, debilitating pain and physical deformity due to the condition. In severe cases treatments for these conditions have used a technique known as fusion with spinal fixation which results in the surgical/mechanical immobilization of areas of the spine and the eventual fusion of the vertebrae in the regions treated. In less severe cases treatment comprises decompression of the affected nerve and fusion of the vertebrae involved.

Spinal fixation procedures use the implantation of screws into the vertebra in the affected region of the spine. Clamp assemblies are attached to the screws. The clamp blocks are, in turn, clamped onto a rod which spans adjacent vertebra and thus fixes the vertebrae relative to each adjacent vertebrae. However, none of the existing spinal fixation systems can be used to directly push, pull or rotate the vertebrae to correct a misalignment of the spine by using top adjusting rotating spindle assemblies.

It is desirable that a clamp system be provided which facilitates pushing, pulling or rotating the vertebrae of the spinal column to realign misaligned vertebrae all from a top access position.

SUMMARY OF THE INVENTION

The present invention relates to a spinal fixation system. The system comprises a screw means for attaching a pivot bolt to a vertebra to be treated. A pivot block spindle assembly is threaded onto the pivot bolt for movement of the pivot block up and down the pivot bolt. The pivot block spindle assembly comprises a body having an aperture, a pivot pin attached to the exterior of the body and an adjusting spindle attached in the aperture of the body, wherein the adjusting spindle rotates independently of the pivot block to thereby move the pivot block up and down the pivot bolt. The system further comprises a rod secured at each of its ends to vertebrae on either side of the vertebra to be treated and a clamp block attached to the rod and the pivot block attached to the clamp block to thereby allow the pivot block spindle to push, pull or rotate the vertebra to be treated. The clamp block comprises an aperture for attaching the clamp block to a rod and a slot for attaching the clamp block to the pivot block spindle assembly.

BRIEF DESCRIPTION OF THE DRAWINGS

Features, aspects and advantages of the invention will be more fully understood when considered with respect to the following detailed description, appended claims and accompanying drawings where:

FIG. 2 is a side view of a sacrum swing bolt screw;

FIG. 3 is a side view of a sacrum swing bolt screw in combination with a swing bolt;

FIG. 4 is a side view of a sacrum swing bolt screw in combination with a swing bolt taken along the line 4—4 of FIG. 3;

FIG. 5 is a side view of a swing bolt;

FIG. 6 is a top view of a reduction block spindle assembly;

FIG. 7 is a side view, in section, of a reduction block spindle assembly taken along the line 7—7 of FIG. 6;

FIG. 8 is a top view of a clamp block;

FIG. 9 is a side view, in section, of the clamp block taken along line 9—9 of FIG. 8;

FIG. 10 is a top view of a pivot block;

FIG. 11 is a side view, in section of the pivot block taken along line 11—11 of FIG. 10;

FIG. 12 is a top view of an adjusting spindle;

FIG. 13 is a side view of the adjusting spindle taken along line 13—13 of FIG. 12;

FIG. 16 is a side view of a portion of a crimping tool;

FIG. 17 is a side view of the crimping tool, taken 90° from the view of FIG. 16.

DETAILED DESCRIPTION

Figure 1:
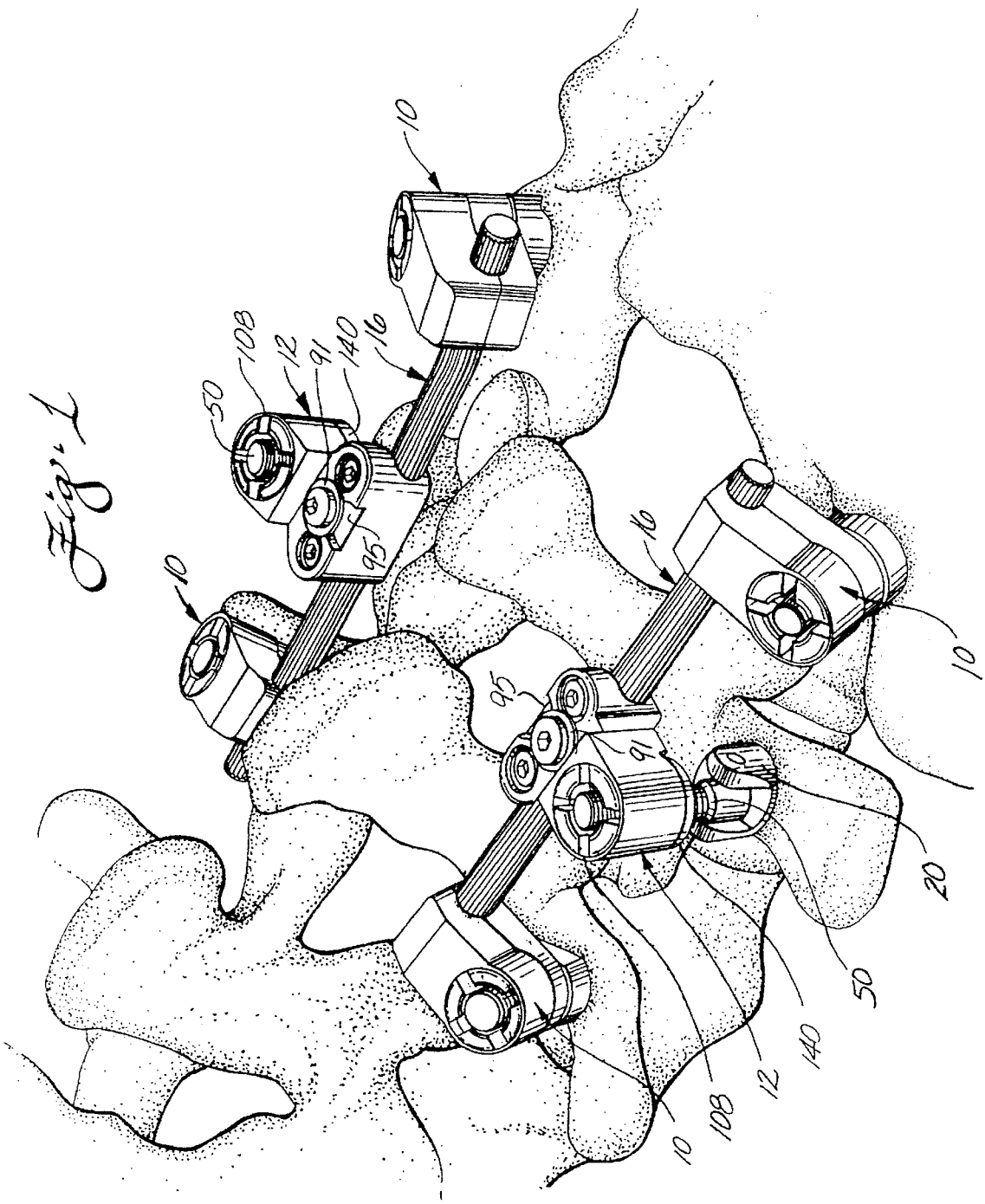
FIG. 1 is a perspective view of a segmental reduction derotation system installed on a section of spine.

The present invention relates to a segmental reduction derotation system (the system; see FIG. 1), comprising clamp assemblies 10 and reduction block spindle assemblies 12 attached to a sacrum swing bolt screw 20 and a swing bolt 50. The clamp assemblies and the reduction block spindle assemblies are connected by a rod 16. Clamps and rods, suitable for use in the present invention are any of the clamps and rods known in the art, but of particular use are the clamps such as the incrementally angled clamps and rods described in U.S. patent application Ser. No. 08/078,724, now U.S. Pat. No. 5,380,323, which is incorporated herein by this reference. The clamps and rods comprise a bracing means. The system is shown, for the purpose of illustration, attached to the 5th lumbar vertebra of the spine.

FIGS. 2–5 show a sacrum swing bolt screw 20 and a swing bolt 50. The sacrum swing bolt screw includes a course-threaded end 22 for placement and attachment of the system into the bony structure of a vertebra of the spine. The preferred location is determined by the surgeon and is usually through the pedicle, although other regions may be used. The screw may be inserted directly into the vertebra or it may be placed in a predrilled opening, dimensioned to receive the threads of the screw firmly in an appropriate support structure of the spine. The configuration of the screw threads is well known in the art and is that which is normally used for screw members intended to be implanted in bone structures.

The upper end of the anchor screw terminates in a shoulder 24. The side of the shoulder distal to the threaded end includes a pair of ears 26 disposed diametrically opposite each other on the perimeter of the shoulder. Each of the ears includes an aperture 28 for insertion of swing bolt pin 29 (see FIG. 3). The screw is pivotally attached via the swing bolt pin to a swing bolt 50.

The swing bolt comprises a threaded section 52 which terminates in a loop 54 having an aperture 56 extending through the loop from one side to the other perpendicular to the longitudinal axis of the swing bolt. The aperture of the loop, when the swing bolt is attached to the sacrum swing bolt screw, aligns with apertures 28 forming an elongated aperture through which swing bolt pin 29 is passed to secure the swing bolt to the sacrum swing bolt screw. The pin is secured in place by use of a press fit relative to aperture 28. Aperture 56 has a slightly wider diameter that of the pin so that the swing bolt can pivot about the pin.

When the system is installed, a reduction block spindle assembly 12 (shown in FIGS. 6–11) is seated on the swing bolt. The reduction block spindle assembly comprises a clamp block 80 and a pivot block 100.

The clamp block (see FIGS. 8–9) has a generally oval shaped cross-section when viewed from the top (FIG. 8). Viewed from the side of the clamp block has a "U"-shaped cross-section and includes an ellipsoid shaped aperture 82 at the base of the "U" (see FIG. 9). Serrations 84, for grasping and mating with serrations of rod 16 are included extending lengthwise along the bottom portion of the inner wall of the ellipsoid shaped aperture. Mating of the serrations in the aperture and on the rod prevents rotation of the clamp block and the pivot block spindle assembly, relative to the rod, once the system is installed.

Perpendicular to, and connecting with, aperture 82 are threaded apertures 86. Threaded apertures 86 are disposed at either end of the oval shaped cross-section of the clamp block. Threaded apertures 86 each accommodate a set screw 88, which, when installed, can be tightened down against the rod to secure the clamp block to the rod. Hexagonal indentations are provided in the top surface of the heads of the set screw so that they can be tightened into place with an allen wrench driver.

Between threaded apertures 86 in the clamp block is disposed a third threaded aperture 90, for accommodating retainer screw 92. The retainer screw secures the clamp block to pivot block 100 when the system is installed. Retainer screw 92 includes a thin flange 91 around the perimeter of the head of the screw (see FIG. 1). Flange 91 extends at least partially over threaded apertures 86 and the set screws installed in the apertures and prevents the set screws from rotating out of the apertures. A hexagonal indentation is also provided in the top surface of the head of the retainer screw to allow it to be threaded into place with a driver.

To prevent retainer screw 92 from rotating and coming loose after it is installed, a recess 95 is provided in the top surface of the clamp block. The recess is disposed adjacent to aperture 90 such that when retainer screw 92 is installed flange 91 partially overlaps the recess. After installation, and adjustment of the system is complete, flange 91 is indented into the recess.

Adjacent to aperture 90, and on one of the "long" sides of the oval shaped cross-section, is a protruding section 93. The protruding section includes slot 94 for attaching the clamp block to pivot block 100 (see FIGS. 8–9). When installed, retainer screw 92 and flange 91 secure the pivot block to the clamp block.

The pivot block 100 (see FIGS. 10–11) comprises a block having a "D"-shaped cross section when viewed from the top. The pivot block includes an aperture 102 extending down through the center of the "D" shaped body. The internal diameter of aperture 102 is stepped. A lower section 104 has one diameter. Adjacent the lower section is an upper section 106, which has a diameter larger than that of the lower section. When assembled, the upper section accommodates the head of an adjusting spindle 120, described below, and the lower section accommodates the shaft of the adjusting spindle. On the flat side of the "D"-shaped pivot block is a "T" shaped pivot 109 that is attached to the body of the pivot block at the base of the "T" and then extends outward therefrom. The pivot slides into slot 94 of the clamp block and thereby attaches the pivot block to the clamp block.

Adjusting spindle 120 (see FIGS. 12–13) has an aperture 122, which is threaded so that it mates with threaded portion 52 of swing bolt 50. The exterior of the adjusting spindle is of different diameters. At lower end 124 of the adjusting spindle, the diameter of the adjusting spindle is at its smallest and this portion of the adjusting spindle extends beyond the lower edge 110 of aperture 102 in the pivot block when the spindle is inserted into that aperture. Adjacent small-diameter portion 124, is an intermediate-diameter portion 126. The intermediate-diameter portion is sized so that it slip fits into the lower section 104 of aperture 102 of the pivot block. Adjacent to the intermediate portion is a large-diameter portion or head 128, which when the adjusting spindle is installed into aperture 102, can rotate freely into section 106 of the pivot block, thus threadably securing the pivot block to the swing bolt once an adjustable spindle flange 140, described below, is attached below the pivot block on the spindle.

Top face 130 of the adjusting spindle includes four radial notches 132, spaced at equal distances about the perimeter of the top face from each other. Each radial notch is located on a radius of the upper surface of the adjusting spindle. The notches align with prongs of a driver, shown in FIGS. 14 and 15 and described in detail below. In one embodiment of the present invention a different driver is attached to a "T" wrench for adjusting the adjusting spindle up or down the swing bolt. The driver is described in detail below.

An adjustable spindle flange ring 140 is assembled to section 124 of the adjusting spindle, after the adjusting spindle has been installed in the pivot block. The flange ring is then electron beam welded to the adjusting spindle. When the adjusting spindle is inserted into the pivot block and the adjusting flange ring is welded in place, the lower face 110 of the pivot block seats next to the adjusting flange ring and the underside face of the large-diameter portion or head of the adjusting spindle which seats next to the upper internal surface of the pivot block. Thus, the adjusting spindle is retained in the pivot block, but because it is not attached to the pivot block, the adjusting spindle can freely rotate in the pivot block when it is threaded up or down on swing bolt 50. Once welded in place, the adjusting flange ring captures the spindle in the pivot block. Thus the pivot block can be moved up or down the swing bolt by rotating the adjusting spindle in the desired direction. Adjusting the adjusting spindle up or down the swing bolt, thereby applies force via the pivot block, the swing bolt and the sacrum swing bolt screw to pull, push or rotate the vertebra to which the sacrum swing bolt screw is attached.

Figure 14:
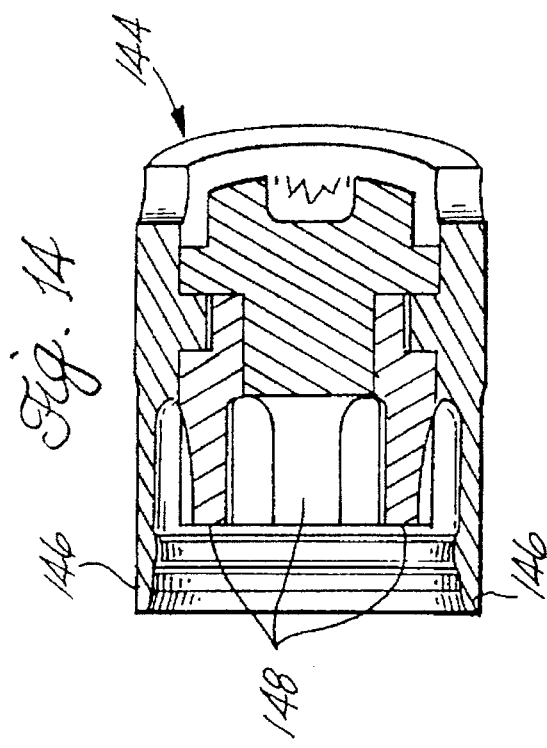
FIG. 14 is a side view, in section of a driver clamp.
Figure 15:
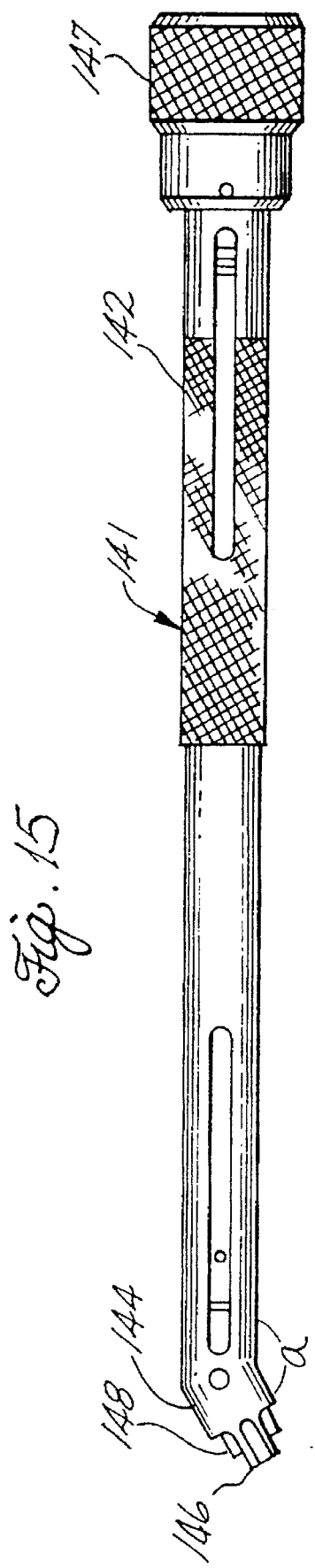
FIG. 15 is a side view of an angled driver.

In one embodiment of the present invention a driver 141 is used to rotate the adjusting spindle 120 along the swing bolt (see FIGS. 14 and 15). The driver comprises a handle 142 and, at one end of the handle, a cylindrical clamp 144. At the other end of the handle is a knob 147. The clamp comprises two holding fingers 146, on the perimeter of the clamp to hold the adjusting spindle for installation onto the swing bolt. Between the holding fingers are four prongs 148, for aligning and mating with the four radial notches 132 of the adjusting spindle. In use an adjusting spindle is snapped into the holding fingers and prongs 148 are aligned with radial notches 132. The driver, with the adjusting spindle attached, is then placed on top of the swing bolt. Knob 147 is then rotated to thread the adjusting bolt onto the swing bolt and to adjust its position. The driver shown is angled by an angle "a" (see FIG. 15) and is useful for use with clamp assemblies which are difficult to access with a straight or non-angled driver. In another embodiment of the present invention (not shown) the driver is not angled, i.e. angle "a" is 180°. This straight driver is useful for most applications where access to the swing bolt is not limited.

After the adjusting spindle has been adjusted during surgery to exert the appropriate pull or push rotation force to the vertebra and is in its desired place, an exposed portion of wall 108 (see FIG. 6) is crimped at one point along its periphery corresponding to one of the radial notches in the adjusting spindle. The crimp ensures that the adjusting spindle is firmly locked in place and that undesired rotation of the adjusting spindle is inhibited after installation of the system.

In one embodiment of the present invention wall 108 is crimped with a tool 160 shown in FIGS. 16 and 17. The tool comprises a handle 162. Attached to the handle, at one end are prongs 164 and 166. In use the prongs 166 are inserted into one set of the radial notches 132 of the adjusting spindle, and between the interior side of wall 108. Prong 164 is placed on the exterior of walls 108. The crimp is made by hitting the opposite end 168 of the handle with a hammer to thereby force prongs 166 down the wall 108 and to thereby deform the wall.

The components of the system, are preferably made of 316 LVM stainless steel, which is electro-polished and passivated to resist corrosion by body fluids. The swing bolt screws come in various lengths and diameters to accommodate the needs of the surgeon in attaching the system to particular vertebrae.

The foregoing describes the structure and interrelations of the parts of the system. A typical installation sequence for the system will now be described.

The first step in the sequence is to install the bracing means clamp assemblies 10 and rods 16, onto anchor screws placed in the vertebrae, or sacrum, on either side of the vertebra to be treated. The clamps and their placement is chosen so that when rod 16 is fastened into the clamps, clamp block 80 which is placed on the rod before hand, can be positioned at the desired alignment for attachment of the system. Clamp block 80 is assembled on the rod before the rod is placed into the clamp assemblies.

A sacrum swing bolt screw assembly is then implanted into the vertebra to be treated. The orientation of the swing bolt, for any vertebra correction is such that the swing bolt swings in a plane perpendicular to the linear rod (see FIG. 1) and allows the pivot block to be oriented at a correct angle to mate with the clamp block. The swing bolt allows the sacrum swing bolt screw to be securely attached to a vertebra, at an angle which is not perpendicular to the rod, while the swing bolt is pivoted into a position to orient the pivot 109 of the pivot block 100 to mate with the slot 94 of the clamp block 80, as described below. A clamp block is then positioned on the rod, in position adjacent to the swing bolt, with the slot of the clamp block aligned with the pivot at the pivot block as the adjusting spindle is rotated down onto the swing bolt. The clamp block is secured in place with set screws 88, by screwing them into threaded apertures 86 after the assembly is complete.

The adjusting spindle is then rotated up the swing bolt to push the vertebra into position, in the case of a correction of kyphosis, or rotated down the swing bolt to pull the vertebra into position, in the case of a correction of spondylolisthesis. In the case of scoliosis, the vertebra is rotated into its correct alignment by pushing one side of the vertebra and pulling the other side of the vertebra to thereby rotate the vertebra relative to the longitudinal axis of the spine.

When the vertebra has been moved into the desired position, wall 108 is crimped to prevent rotation of the adjusting spindle, the set screws 88 are re-tightened and flange 91 is indented into recess 95 to prevent rotation of the retaining screw.

The present invention is not limited to the specific designs shown. For example, the crimping tool and driver described are not limited for use with the clamp assembly of the present invention. It will be clear to those skilled in the art that the crimping tool and driver could be used with other clamps which include a nut type element which includes radial notches in its upper surface. Therefore, the present invention is not intended to be limited to the working embodiments described above. The scope of the invention is defined in the following claims.

What is claimed is:

1. A method for pushing, pulling or rotating a misaligned vertebra to thereby move the vertebra into correct alignment with the spine comprising:

attaching a screw to the vertebra to be treated;

attaching a bolt to the screw, wherein the bolt rotates in an arc on the screw;

attaching each end of a rod to vertebrae on either side of the vertebra to be treated;

attaching the bolt to an adjusting spindle; and attaching the adjusting spindle to the rod.

2. A method as recited in claim 1 wherein the rod is attached to vertebrae on either side of the vertebra to be treated by clamps attached to vertebrae anchor screws.

3. A method as recited in claim 1 wherein the adjusting spindle is pivotally attached to the rod by the steps comprising:

attaching a clamp to the rod;

attaching a pivot block to the clamp; and attaching the pivot block to the adjusting spindle.

4. A method for pushing, pulling or rotating a misaligned vertebra to thereby move the vertebra into correct alignment with the spine comprising:

attaching a screw to the vertebra to be treated;

attaching a bolt to the screw, wherein the bolt rotates in an arc on the screw;

attaching each end of a rod to vertebrae on either side of the vertebra to be treated; and attaching the bolt to the rod so that the bolt is movable relative to the rod to thereby elevate, lower or rotate the vertebra attached to the bolt relative to the rod wherein the bolt is made movable relative to the rod by the steps comprising:

inserting an adjusting spindle into a pivot block so that the adjusting spindle rotates independently of the pivot block;

threading the adjusting spindle and pivot block onto the bolt; and attaching the pivot block to the rod.

* * * * *